US010722875B2

(12) United States Patent
Lee et al.

(10) Patent No.: US 10,722,875 B2
(45) Date of Patent: Jul. 28, 2020

(54) ZINC-IMIDAZOLE COMPLEX MIXED CATALYST AND METHOD FOR PRODUCING METHYL N-PHENYL CARBAMATE USING THE SAME

(71) Applicant: KOREA INSTITUTE OF SCIENCE AND TECHNOLOGY, Seoul (KR)

(72) Inventors: Hyun Joo Lee, Seoul (KR); Jungho Jae, Seoul (KR); Hong Gon Kim, Seoul (KR); Deliana Dahnum, Seoul (KR); Shinhye Cho, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 16/196,549

(22) Filed: Nov. 20, 2018

(65) Prior Publication Data
US 2020/0061596 A1    Feb. 27, 2020

(30) Foreign Application Priority Data

Aug. 27, 2018    (KR) .................... 10-2018-0100230

(51) Int. Cl.
B01J 31/18    (2006.01)
C07F 3/06    (2006.01)
(Continued)

(52) U.S. Cl.
CPC ......... B01J 31/1825 (2013.01); B01J 31/181 (2013.01); B01J 37/0236 (2013.01); B01J 37/031 (2013.01); C07C 269/04 (2013.01); C07F 3/06 (2013.01); B01J 2231/4283 (2013.01); B01J 2531/26 (2013.01)

(58) Field of Classification Search
None
See application file for complete search history.

(56) References Cited

U.S. PATENT DOCUMENTS 3,763,217 A    10/1973 Brill et al.
4,268,683 A    5/1981 Gurgiolo et al.
(Continued)

FOREIGN PATENT DOCUMENTS

FR    2978442 A1 *    2/2013    ............... C07F 3/06
KR    20170118460    * 10/2017
(Continued)

OTHER PUBLICATIONS

Shi ("A single precursor approach for ZIF synthesis . . . " CrystEngComm, 17, 2015, p. 3998-4005, including SI p. S1-S10) (Year: 2015).*

(Continued)

Primary Examiner — Amy C Bonaparte
(74) Attorney, Agent, or Firm — Rabin & Berdo, P.C.

(57) ABSTRACT

Disclosed is a zinc-imidazole complex mixed catalyst. Also disclosed are a method for preparing the zinc-imidazole complex mixed catalyst and a method for producing a methyl N-phenyl carbamate in high yield with high selectivity in the presence of the catalyst. The zinc-imidazole complex mixed catalyst can be reused due to its high reaction stability. In addition, the use of the zinc-imidazole complex mixed catalyst leads to a marked improvement in the production yield of a methyl N-phenyl carbamate with high selectivity.

5 Claims, 5 Drawing Sheets

(51) Int. Cl.
*C07C 269/04* (2006.01)
*B01J 37/03* (2006.01)
*B01J 37/02* (2006.01)

(56) References Cited

U.S. PATENT DOCUMENTS

| | | | | |
|---|---|---|---|---|
| 5,698,731 | A | * 12/1997 | Bosetti | C07C 269/04 560/24 |
| 2012/0041223 | A1 | * 2/2012 | Wershofen | C07C 269/04 560/24 |
| 2016/0244606 | A1 | * 8/2016 | Ravichandran | C09J 167/00 |

FOREIGN PATENT DOCUMENTS

| KR | 10-1865817 B1 | 6/2018 | |
|---|---|---|---|
| WO | WO 2018210711 | * 11/2018 | |

OTHER PUBLICATIONS

Zhao ("Synthesis of Methyl N-Phenyl Carbamate Catalyzed by Ionic Liquid-Promoted Zinc Acetate" Industrial and Engineering Chemistry Research, 2012, 5, p. 11335-11340) (Year: 2012).*

Xue ("Direct Synthesis of 7nm-Thick Zinc(II)-Benzimidazole-Acetate Metal-Organic Framework Nanosheets" Chemistry of Materials, 2018 (first published Dec. 9, 2017), 30, p. 69-73, including Supporting Information p. S1-S15) (Year: 2017).*

G. Del Angel et al., "Effect of HC1 acid on the hydrodechlorination of chlorobenzene over palladium supported catalysts", Journal of Molecular Catalysis A: Chemical, 2001, pp. 9-13, vol. 165.

Feng Shi et al., "Developing effective catalyst system for reductive carbonylation of nitrobenzene based on the diversity of ionic liquids", Journal of Molecular Catalysis A: Chemical, 2006, pp. 64-67, vol. 244.

Masayoshi Honda et al., "Heterogeneous $CeO_2$ catalyst for the one-pot synthesis of organic carbamates from amines, $CO_2$ and alcohols", Green Chem., 2011, pp. 3406-3413, vol. 13.

Hoon Sik Kim et al., "Oxidative Carbonylation of Aromatic Amines by Selenium Compounds", Journal of Catalysis, 1999, pp. 526-534, vol. 184.

Fang Li et al., "Investigation of supported $Zn(OAc)_2$ catalyst and its stability in N-phenyl carbamate synthesis", Applied Catalysis A: General, 2014, pp. 355-362, vol. 475.

Fang Li et al., "Synthesis of Methyl N-Phenyl Carbamate from Aniline and Dimethyl Carbonate over Supported Zirconia Catalyst", Ind. Eng. Chem. Res., 2006, pp. 4892-4897, vol. 45.

Lifeng Zhang et al., "Experimental and theoretical investigation of reaction of aniline with dimethyl carbonate catalyzed by acid-base bifunctional ionic liquids", Catalysis Today, 2010, pp. 279-285, vol. 158.

Xiang Wang et al., "Rapid and Cost-Effective Synthesis of Nanosized Zeolitic Imidazolate Framework-7 with N,N'-Dimethylformamide as Solvent and Metal Acetate Salt as Metal Source", CHEMPLUSCHEM, Apr. 29, 2014, pp. 1-8.

Feng Xue et al., "Direct Synthesis of 7 nm-Thick Zinc (II)—Benzimidazole—Acetate Metal-Organic Framework Nanosheets", Chemistry of Materials, Dec. 9, 2017, pp. 69-73, vol. 30.

* cited by examiner

ZINC-IMIDAZOLE COMPLEX MIXED CATALYST AND METHOD FOR PRODUCING METHYL N-PHENYL CARBAMATE USING THE SAME

CROSS-REFERENCE TO RELATED APPLICATIONS

This application claims priority under 35 U.S.C. § 119 to Korean Patent Application No. 10-2018-0100230 filed on Aug. 27, 2018 in the Korean Intellectual Property Office, the disclosure of which is incorporated herein by reference in its entirety.

BACKGROUND OF THE INVENTION

1. Field of the Invention

The present invention relates to a method for producing a methyl N-phenyl carbamate using a zinc-imidazole complex mixed catalyst, and more specifically to a technology for preparing a zinc-imidazole complex mixed catalyst and producing a methyl N-phenyl carbamate in high yield with high selectivity in the presence of the catalyst.

2. Description of the Related Art

Aromatic carbamates are valuable intermediates that are used in the production of herb medicines, dyes, pharmaceuticals, and isocyanates as units for polyurethane synthesis.

Isocyanates as monomers for polyurethanes are usually produced by reacting corresponding amines with phosgene. However, the reactant phosgene is known as a highly toxic substance that causes environmental pollution and safety problems. Under such circumstances, methods for producing isocyanates without using phosgene have been investigated in various aspects. Reductive carbonylation of nitrobenzene [J. Mol. Catal. A: Chem. (2001) 9; J. Mol. catal. A: Chem. (2006) 64], oxidative carbonylation of aniline [Green Chem. (2011) 3406; J. Catal. (1999) 526], and methoxycarbonylation of amines with dimethyl carbonate (U.S. Pat. No. 4,268,683) are known as typical methods for isocyanate production without using phosgene. The products of these methods are aromatic carbamates that can be used to synthesize isocyanates through thermal decomposition.

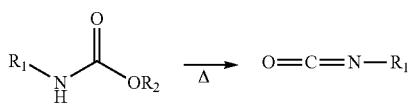

Reductive carbonylation of nitrobenzene and oxidative carbonylation of aniline are limited in that carbon monoxide (CO), which is also a toxic gas, is used, high temperature (130-250° C.) and high pressure (40-80 bar) conditions are required, and noble metal catalysts (Ru, Pd, Rh, and Se) are used. In contrast, methoxycarbonylation of amines with dimethyl carbonate is advantageous in that the reaction proceeds under milder conditions and environmentally friendly dimethyl carbonate is used.

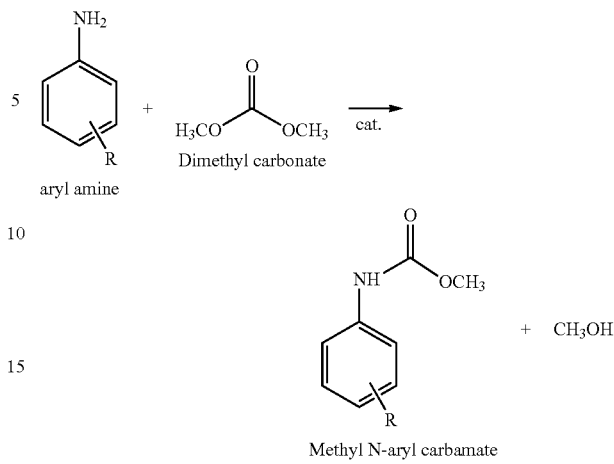

In addition, methoxycarbonylation of amines with dimethyl carbonate produces methanol as a by-product, which can be reused for dimethyl carbonate production through oxidative carbonylation. Representative catalysts for this method are relatively inexpensive metals such as Zn and Pb.

U.S. Pat. No. 3,763,217 describes a method for preparing a carbamate by reacting an amine with an alkyl carbonate under reflux in the presence of a Lewis acid catalyst such as uranyl nitrate. However, this method requires a long reaction time of 18-24 hours and has the problems of low conversion rate and selectivity (~20%).

Further, U.S. Pat. No. 4,268,683 reported a method for synthesizing a carbamate using a halide or an organic acid salt of Sn(II) or Zn(II) as a Lewis acid catalyst. Particularly, the use of zinc acetate as a catalyst for methyl N-phenyl carbamate synthesis achieved a selectivity of 99.8% at a temperature of 140° C. and a pressure of 0.88 MPa. However, according to a study conducted by Feng Li et al., the use of zinc acetate for methyl N-phenyl carbamate production suffers from difficulty in separating and recovering the product and the zinc acetate is converted to zinc oxide by reaction with by-produced methanol, losing its catalytic activity (Applied Catalysis A: General 475 (2014) 355).

In attempts to solve these problems, heterogeneous catalysts such as Al/MCM-41, ZnO—$TiO_2$, and $ZrO_2/SiO_2$ were developed (Ind. Eng. Chem. Res. 2006, 45, 4892). However, the yields are still limited to ~60-80% and a detailed description of the reuse of the catalysts is not sufficiently found in the literature.

Zeolitic imidazole frameworks (ZIFs) are structures produced from Zn compounds and imidazole compounds. ZIFs are structurally similar to zeolite and have good thermal stability and large surface area. ZIFs are generally used in membranes for the separation of $CO_2$, hydrogen, and methane, $EO/CO_2$ coupling, and transesterification. However, to our knowledge, attempts to produce methyl N-phenyl carbamates using ZIFs have never been reported to date.

The present inventors have found that a zinc-imidazole complex mixed catalyst prepared in a one-pot process can be used as a reusable catalyst for methyl N-phenyl carbamate production.

The present invention has been accomplished based on this finding.

PRIOR ART DOCUMENTS

Patent Documents (Patent Document 1) U.S. Pat. No. 3,763,217
(Patent Document 2) U.S. Pat. No. 4,268,683

Non-Patent Documents (Non-Patent Document 1) Fang Li et. al. Appl. Catal. A: Gen., 475, 355-362 (2014)
(Non-Patent Document 2) Zhangg L et. al. Catalysis Today, 158, 279-285 (2010)

SUMMARY OF THE INVENTION

The present invention has been made in view of the above problems, and it is one object of the present invention to provide a zinc-imidazole complex mixed catalyst that can be reused due to its high reaction yield and good stability, and a method for preparing the catalyst.

It is a further object of the present invention to provide a method for producing a methyl N-phenyl carbamate in high yield with high selectivity in the presence of the zinc-imidazole complex mixed catalyst.

According to one representative aspect of the present invention, there is provided a zinc-imidazole complex mixed catalyst including a first zinc-imidazole complex and a second zinc-imidazole complex wherein the first zinc-imidazole complex is represented by Formula 1:

$$Zn(A)_{x'} \quad (1)$$

wherein A is represented by Formula 3 or 4:

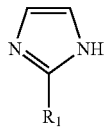

(3)

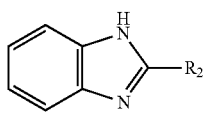

(4)

(wherein $R_1$ and $R_2$ may be identical to or different from each other and are each independently a hydrogen atom, a methyl group, a chloromethyl group, a phenyl group or a carboxyl group) and x' is a rational number from 1 to 2, and wherein the second zinc-imidazole complex is represented by Formula 2:

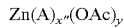

$$Zn(A)_{x''}(OAc)_y \quad (2)$$

wherein A is as defined in Formula 1 and x" and y may be identical to or different from x' and are each independently a rational number from 1 to 2.

Preferably, x' is 2, x" is 1, and y is 1.

According to a further representative aspect of the present invention, there is provided a method for preparing the zinc-imidazole complex mixed catalyst including the first zinc-imidazole complex represented by Formula 1 and the second zinc-imidazole complex represented by Formula 2, the method including (A) reacting a zinc precursor with an imidazole precursor and (B) activating the reaction mixture.

Preferably, in step (A), a zinc precursor is mixed with an imidazole precursor in a first solvent and the mixture is allowed to react at a temperature of 100 to 150° C. for 12 to 48 hours.

Preferably, in step (B), the reaction mixture is precipitated in a second solvent and the precipitate is collected and dried at a temperature of 180 to 200° C. for 1 to 5 hours.

The zinc precursor is preferably a zinc salt, more preferably zinc acetate.

The imidazole precursor is preferably selected from imidazole, 2-chloromethylimidazole, imidazole-2-carboxylic acid, 2-phenylimidazole, benzimidazole, 2-methylimidazole, and mixtures thereof.

The zinc precursor is preferably allowed to react with the imidazole precursor in a molar ratio of 1:1-4.

Preferably, the first solvent and the second solvent may be the same as or different from each other and are each independently selected from N,N-dimethylformamide, N,N-dimethylacetamide, N-methyl-2-pyrrolidone, N-ethyl-2-pyrrolidone, vinylpyrrolidone, 1,3-dimethyl-2-imidazolidinone, dimethyl sulfoxide, hexamethylphosphoramide, and mixtures thereof.

According to another representative aspect of the present invention, there is provided a method for producing a methyl N-phenyl carbamate, including (C) reacting an aromatic amine with dimethyl carbonate in the presence of the zinc-imidazole complex mixed catalyst.

The reaction is preferably carried out at a temperature of 100 to 250° C. for 1 to 5 hours.

The aromatic amine is preferably allowed to react with the dimethyl carbonate in a molar ratio of 1:5-40.

The zinc-imidazole complex mixed catalyst is preferably added in an amount of 1 to 20% by weight, based on the weight of the aromatic amine.

The aromatic amine is preferably selected from aniline, phenylenediamine, methylenediphenyldiamine, toluenediamine, and mixtures thereof.

Exemplary embodiments of the present invention enable the preparation of a zinc-imidazole complex mixed catalyst that can be reused due to its high reaction stability.

In addition, the use of the zinc-imidazole complex mixed catalyst leads to a marked improvement in the production yield of a methyl N-phenyl carbamate with high selectivity.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
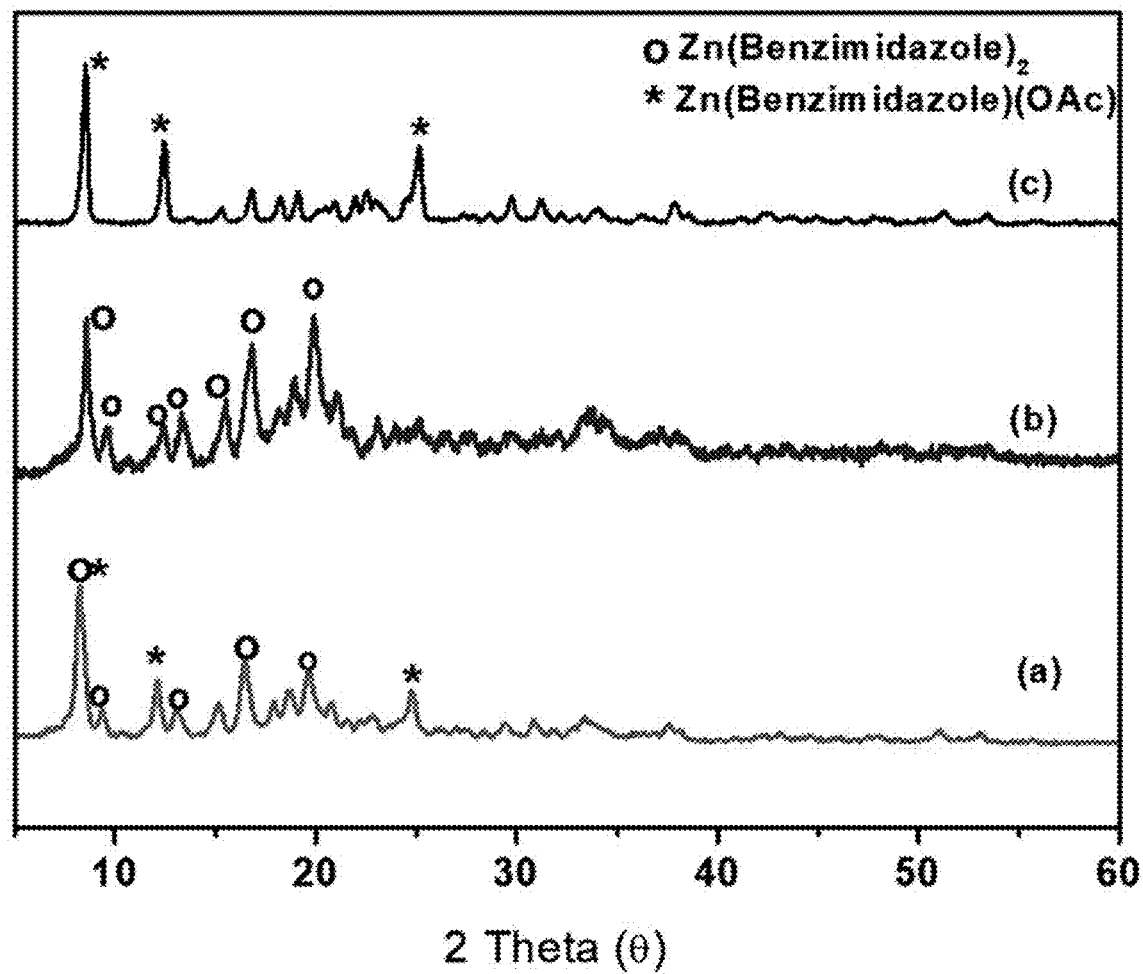
FIG. 1 shows X-ray diffraction patterns of (a) a zinc-imidazole complex mixed catalyst including Zn(benzimidazole)$_2$ and Zn(benzimidazole)OAc in a ratio of 1:1, which was prepared in one pot in Preparative Example 5, (b) Zn(benzimidazole)$_2$, and (c) Zn(benzimidazole)(OAc)

Several aspects and various embodiments of the present invention will now be described in more detail.

One aspect of the present invention provides a zinc-imidazole complex mixed catalyst including a first zinc-imidazole complex and a second zinc-imidazole complex wherein the first zinc-imidazole complex is represented by Formula 1:

  (1)

wherein A is represented by Formula 3 or 4:

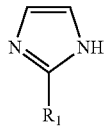  (3)

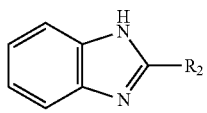  (4)

(wherein $R_1$ and $R_2$ may be identical to or different from each other and are each independently a hydrogen atom, a methyl group, a chloromethyl group, a phenyl group or a carboxyl group) and x' is a rational number from 1 to 2, and wherein the second zinc-imidazole complex is represented by Formula 2:

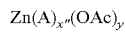  (2)

wherein A is as defined in Formula 1 and x" and y may be identical to or different from x' and are each independently a rational number from 1 to 2.

More preferably, x' is 2, x" is 1, and y is 1.

The zinc-imidazole complex mixed catalyst of the present invention can be used for the production of a methyl N-phenyl carbamate and can be used for the reaction of an aromatic amine and dimethyl carbonate.

A further aspect of the present invention provides a method for preparing a zinc-imidazole complex mixed catalyst including (A) reacting a zinc precursor with an imidazole precursor and (B) activating the reaction mixture wherein the zinc-imidazole complex mixed catalyst includes a first zinc-imidazole complex represented by Formula 1:

  (1)

wherein A is represented by Formula 3 or 4:

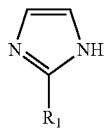  (3)

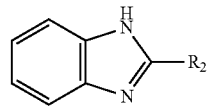  (4)

(wherein $R_1$ and $R_2$ may be identical to or different from each other and are each independently a hydrogen atom, a methyl group, a chloromethyl group, a phenyl group or a carboxyl group) and x' is a rational number from 1 to 2, and a second zinc-imidazole complex represented by Formula 2:

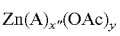  (2)

wherein A is as defined in Formula 1 and x" and y may be identical to or different from x' and are each independently a rational number from 1 to 2.

In step (A), a zinc precursor is mixed with an imidazole precursor in a first solvent and the mixture is allowed to react in an open space at a temperature of 100 to 150° C. for 12 to 48 hours. The reaction temperature lower than 100° C. may be insufficient for the reaction to proceed due to insufficient chemical bonding energy between the zinc precursor and the imidazole precursor. Meanwhile, the reaction temperature exceeding 150° C. may cause deformation of the organic compound imidazole.

The zinc precursor is preferably a zinc salt. The zinc salt is preferably selected from zinc acetate, zinc nitrate, zinc oxalate, zinc halides, and mixtures thereof. More preferably, the zinc salt is zinc acetate ($Zn(OAc)_2$).

The imidazole precursor is preferably selected from imidazole, 2-chloromethylimidazole, imidazole-2-carboxylic acid, 2-phenylimidazole, benzimidazole, 2-methylimidazole, and mixtures thereof.

The first solvent is preferably a polar compound having a boiling point of at least 150° C. More preferably, the first solvent is selected from N,N-dimethylformamide, N,N-dimethylacetamide, N-methyl-2-pyrrolidone, N-ethyl-2-pyrrolidone, vinylpyrrolidone, 1,3-dimethyl-2-imidazolidinone, dimethyl sulfoxide, hexamethylphosphoramide, and mixtures thereof.

The zinc precursor is preferably allowed to react with the imidazole precursor in a molar ratio of 1:1-4 for the synthesis of the mixed catalyst. As described previously, the zinc precursor may be a zinc salt. When the imidazole precursor is allowed to react with the zinc salt in an equivalent ratio of 4:1, the first zinc-imidazole complex and the second zinc-imidazole complex can be prepared in a one-pot process. A conventional zinc-imidazole framework (ZIF) forms an ideal structure in which zinc and imidazole are present in a 1:2 ratio. In this framework, the Lewis acid sites of zinc are completely hindered by imidazole. In contrast, according to the method of the present invention, the equivalent ratio of the imidazole to the zinc is limited to <4:1 to induce the synthesis of a combination of the first zinc-imidazole complex and the second zinc-imidazole complex.

In step (B), the reaction mixture is activated. Specifically, the reaction mixture is precipitated in a second solvent and the precipitate is collected and dried at a temperature of 180 to 200° C. for 1 to 5 hours. Outside the drying temperature and time ranges, there is a risk that satisfactory activation of the reaction mixture may not be achieved.

The second solvent may be the same as or different from the first solvent. Specifically, the second solvent is selected from N,N-dimethylformamide, N,N-dimethylacetamide, N-methyl-2-pyrrolidone, N-ethyl-2-pyrrolidone, vinylpyrrolidone, 1,3-dimethyl-2-imidazolidinone, dimethyl sulfoxide, hexamethylphosphoramide, and mixtures thereof.

The polar first solvent may remain attached to the surface of the catalytically active species even after the reaction. The activation step is carried out to remove the attached polar solvent from the catalytically active species. The activation solvent is an aromatic amine or diamine used for methoxycarboxylation and corresponds to the imidazole precursor. That is, the reactant imidazole precursor is used as the activation solvent, thus avoiding the need for subsequent washing. This is effective in terms of processing and cost.

The most preferred conditions for the method of the present invention are as follow: (i) the zinc precursor is mixed with the imidazole precursor in the first solvent and the mixture is allowed to react in an open space at a temperature of 100 to 150° C. for 12 to 48 hours (step (A)); (ii) N,N-dimethylformamide is used as the first and second solvents; and (iii) the zinc precursor is allowed to react with the imidazole precursor in a molar ratio of 1:1-4. When the conditions (i) and (iii) are all met, the use of the resulting catalyst for methyl N-phenyl carbamate production drastically reduces the total yield of methylation by-products to less than 5%. If one or more of the conditions (i) to (iii) are not met, the total yield of methylation by-products is 20% or more, which is at least four times higher than that obtained when the catalyst prepared under the conditions defined above is used.

Another aspect of the present invention provides a method for producing a methyl N-phenyl carbamate, including (C) reacting an aromatic amine with dimethyl carbonate in the presence of the zinc-imidazole complex mixed catalyst.

The reaction is preferably carried out at a temperature of 90 to 250° C. for 1 to 5 hours. If the reaction temperature is lower than 90° C., the production of a sufficient amount of the desired methyl N-phenyl carbamate cannot be expected. As the reaction temperature decreases, the reaction time increases undesirably. Outside the temperature and time ranges, the production yield of the desired product is considerably lowered. More preferably, the reaction is carried out at a temperature of 150 to 250° C. for 1 to 2 hours. Within these ranges, the highest yield of the desired product is obtained.

The aromatic amine is preferably selected from aniline, phenylenediamine, methylenediphenyldiamine, toluenediamine, and mixtures thereof.

The molar ratio of the aromatic amine to the dimethyl carbonate is preferably in the range of 1:5-40. Within this range, the yield of the desired product is markedly improved. Outside this range, an increase in yield by the action of the catalyst cannot be expected.

The dimethyl carbonate acts as a methylation agent in the reaction with the aromatic amine. Various methylation products are synthesized through the following reaction pathways.

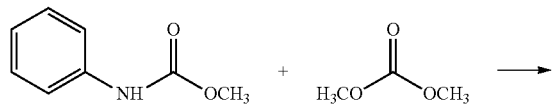

(1)

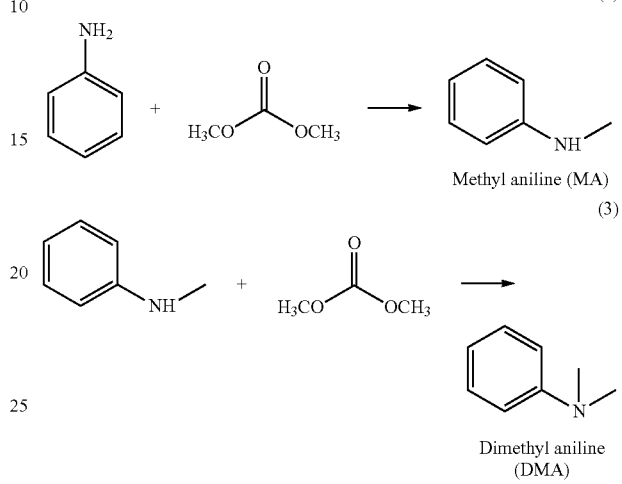

Methyl N-methyl phenyl carbamate (MMPC)

(2)

Methyl aniline (MA)

(3)

Dimethyl aniline (DMA)

According to the present invention, the total yield of the methylation products can be limited to less than 5%, as described previously.

The zinc-imidazole complex mixed catalyst is preferably added in an amount ranging from 1 to 20% by weight, based on the weight of the aromatic amine. Outside this range, the yield of the desired methyl N-phenyl carbamate is considerably lowered. More preferably, the amount of the zinc-imidazole complex mixed catalyst is in the range of 5 to 15% by weight, based on the weight of the aromatic amine. Within this range, the yield of the desired product is kept constant or increases.

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not explicitly presented. Such modifications and variations are intended to come within the scope of the appended claims.

The experimental results of the following examples, including comparative examples, are merely representative and the effects of the exemplary embodiments of the present invention that are not explicitly presented hereinafter can be specifically found in the corresponding sections.

Preparative Example 1: Synthesis of Zinc-Imidazole Complex Mixed Catalyst (1)

60 g of N,N-dimethylformamide as a solvent and $Zn(OAc)_2$ and benzimidazole in a molar ratio of 1:1.5 were placed in a flask. The reaction was allowed to proceed at 130° C. for 24 h. The resulting solid was collected by filtration. The solid was precipitated in N,N-dimethylformamide, collected, and dried under vacuum at 180° C. for 3 h to afford $Zn(benzimidazole)_{1.6}(OAc)_{0.4}$ as a zinc-imidazole complex mixed catalyst.

Figure 2:
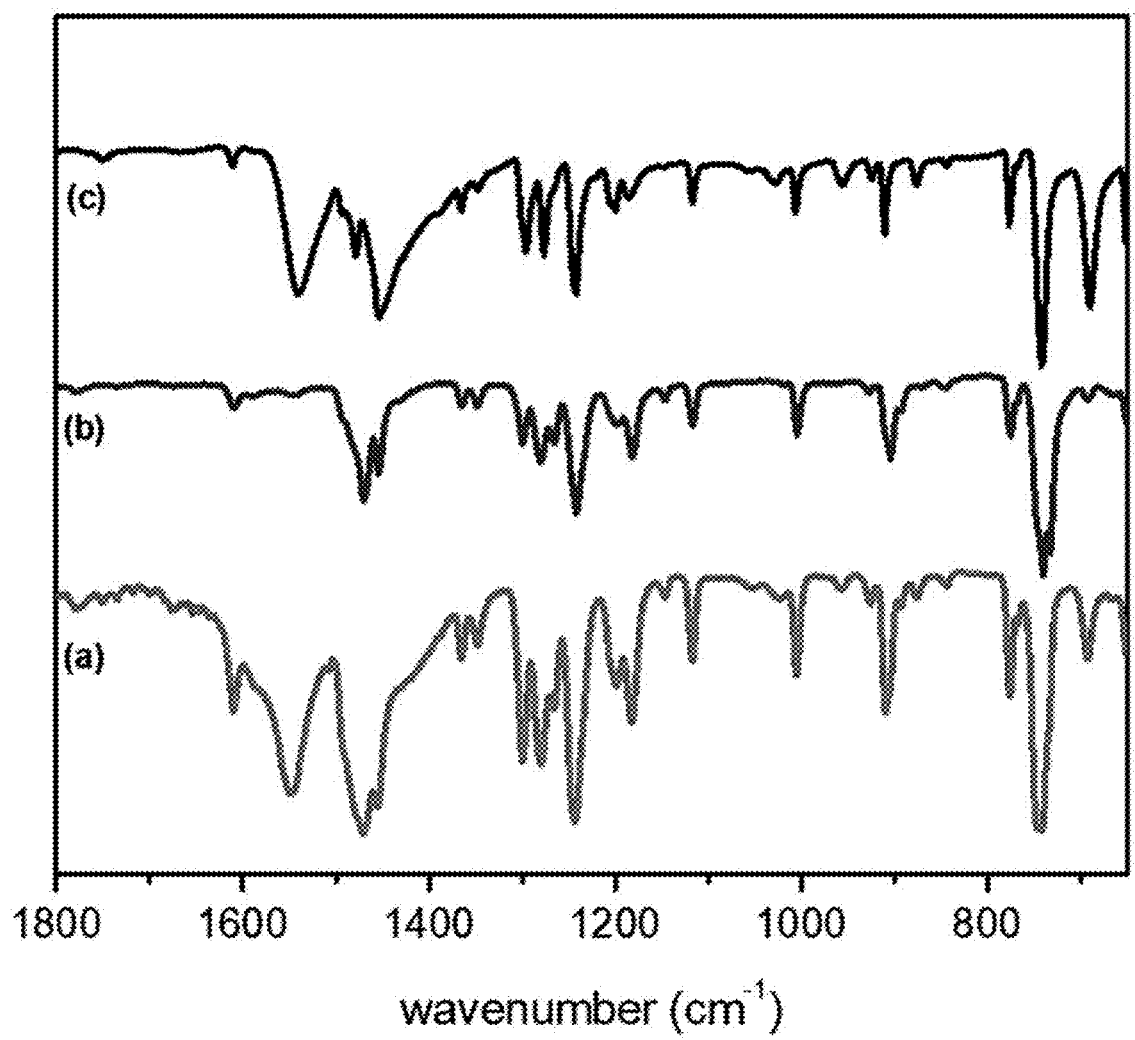
FIG. 2 shows Fourier transform infrared (FT-IR) spectra of (a) a zinc-imidazole complex mixed catalyst including Zn(benzimidazole)$_2$ and Zn(benzimidazole)OAc in a ratio of 1:1, which was prepared in one pot in Preparative Example 5, (b) Zn(benzimidazole)$_2$, and (c) Zn(benzimidazole)(OAc)
Figure 3:
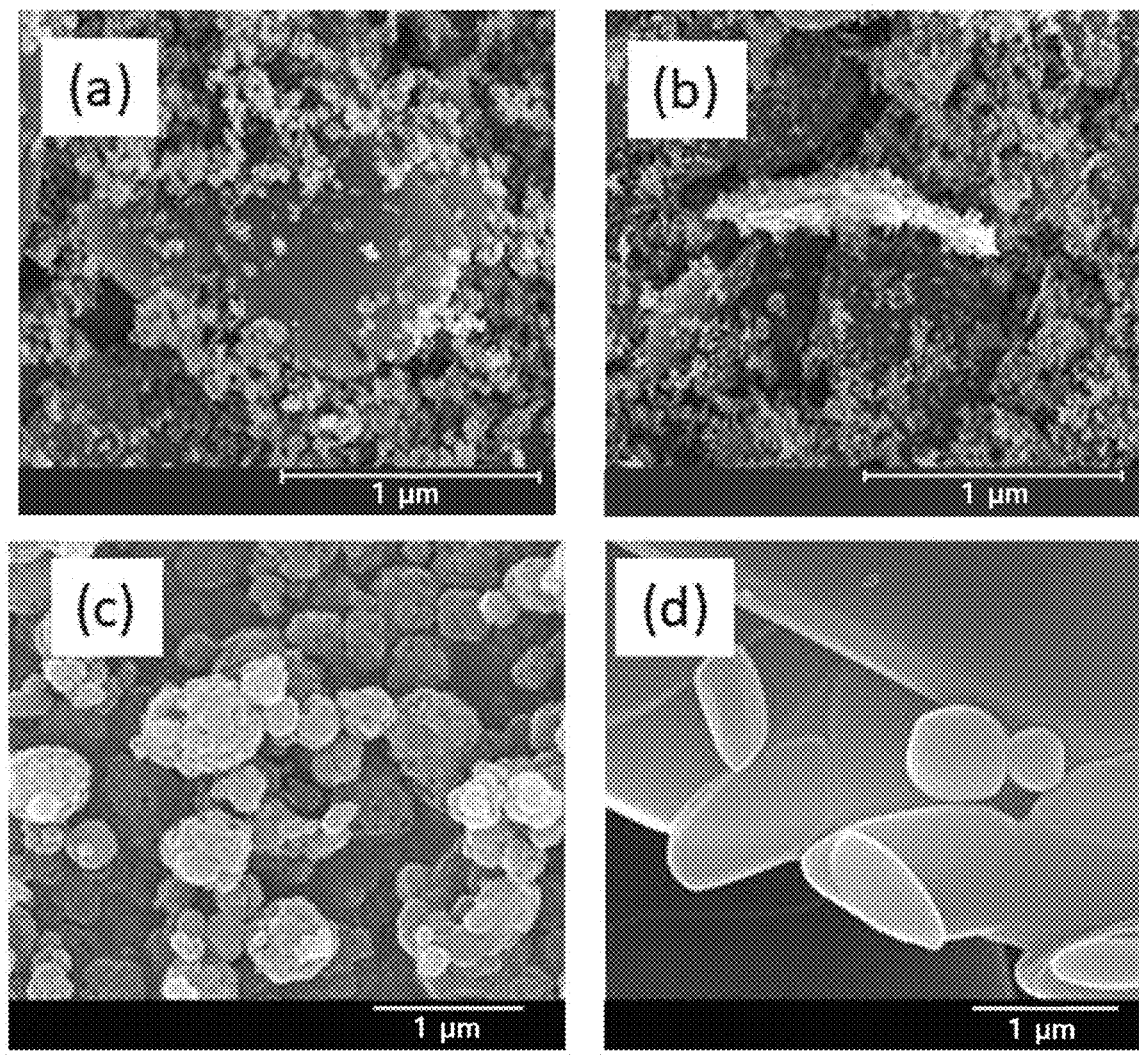
FIG. 3 shows of SEM images of (a) and (b) a zinc-imidazole complex mixed catalyst including Zn(benzimidazole)$_2$ and Zn(benzimidazole)OAc in a ratio of 1:1, which was prepared in one pot in Preparative Example 5, (c) Zn(benzimidazole)$_2$, and (d) Zn(benzimidazole)(OAc)

The catalyst was analyzed by Fourier-transform infrared (IR) spectroscopy and X-ray diffraction (XRD) and the results are shown in FIGS. 1-3.

Preparative Examples 2-5: Synthesis of Zinc-Imidazole Complex Mixed Catalysts (2)

Zinc-imidazole complex mixed catalysts were synthesized in the same manner as in Preparative Example 1, except that imidazole (Preparative Example 2), 2-chloromethylimidazole (Preparative Example 3), imidazole-2-carboxylic acid (Preparative Example 4), and 2-phenylimidazole (Preparative Example 5) were used instead of benzimidazole and the reaction conditions were changed as shown in Table 1.

TABLE 1

| Preparative Example No. | Imidazole | Reaction temp. (° C.) | Reaction time (h) | Product |
|---|---|---|---|---|
| Preparative Example 2 | Imidazole | 150 | 24 | Zn(imidazole)$_2$ + Zn(imidazole)OAc |
| Preparative Example 3 | 2-Chloromethylimidazole | 150 | 12 | Zn(2-chloromethylimidazole)$_2$ + Zn(2-chloromethylimidazole)OAc |
| Preparative Example 4 | Imidazole-2-carboxylic acid | 150 | 36 | Zn(imidazole-2-carboxylic acid)$_2$ + Zn(imidazole-2-carboxylic acid)OAc |
| Preparative Example 5 | 2-Phenylimidazole | 150 | 48 | Zn(2-phenylimidazole)$_2$ + Zn(2-phenylimidazole)OAc |

Preparative Examples 6-9: Synthesis of Zinc-Imidazole Complex Mixed Catalysts (3)

Zinc-imidazole complex mixed catalysts were prepared in the same manner as in Preparative Example 1, except that the molar ratio of Zn(OAc)$_2$ and benzimidazole and the reaction conditions were changed as shown in Table 1.

TABLE 2

| Preparative Example No. | Zn(OAc)$_2$:benzimidazole molar ratio | Reaction temp. (° C.) | Reaction time (h) | Zn(benzimidazole)$_2$:Zn(benzimidazole)OAc in the product |
|---|---|---|---|---|
| Preparative Example 6 | 1:1.1 | 150 | 12 | 0.1:0.9 |
| Preparative Example 7 | 1:1.7 | 150 | 12 | 0.3:0.7 |
| Preparative Example 8 | 1:2 | 150 | 12 | 0.2:0.8 |
| Preparative Example 9 | 1:4 | 150 | 12 | 0.05:0.95 |

Examples 1-5: Production of Methyl N-Phenyl Carbamate (1)

Methyl N-phenyl carbamate was produced using the zinc-imidazole complex mixed catalysts synthesized in Preparative Examples 1-5 by the following procedure. The reaction is shown as follows:

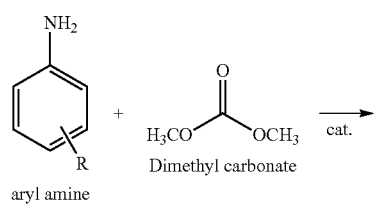

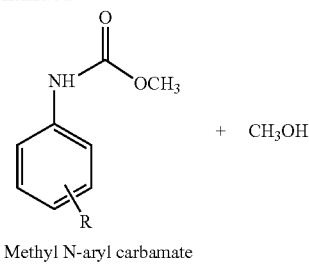

Methyl N-aryl carbamate

First, 0.11 g of each of the catalysts and 13.5 g (150 mmol) of dimethyl carbonate were placed in a batch reactor, and then 1.16 g (12.5 mmol) of aniline as a reactant was added thereto. The amount of the catalyst corresponded to 10 wt %, based on the weight of the aniline. The temperature of the reactor was raised to 190° C. The reaction was allowed to proceed with stirring at a rate of 500 rpm for 2 h to produce methyl N-phenyl carbamate.

Figure 4:
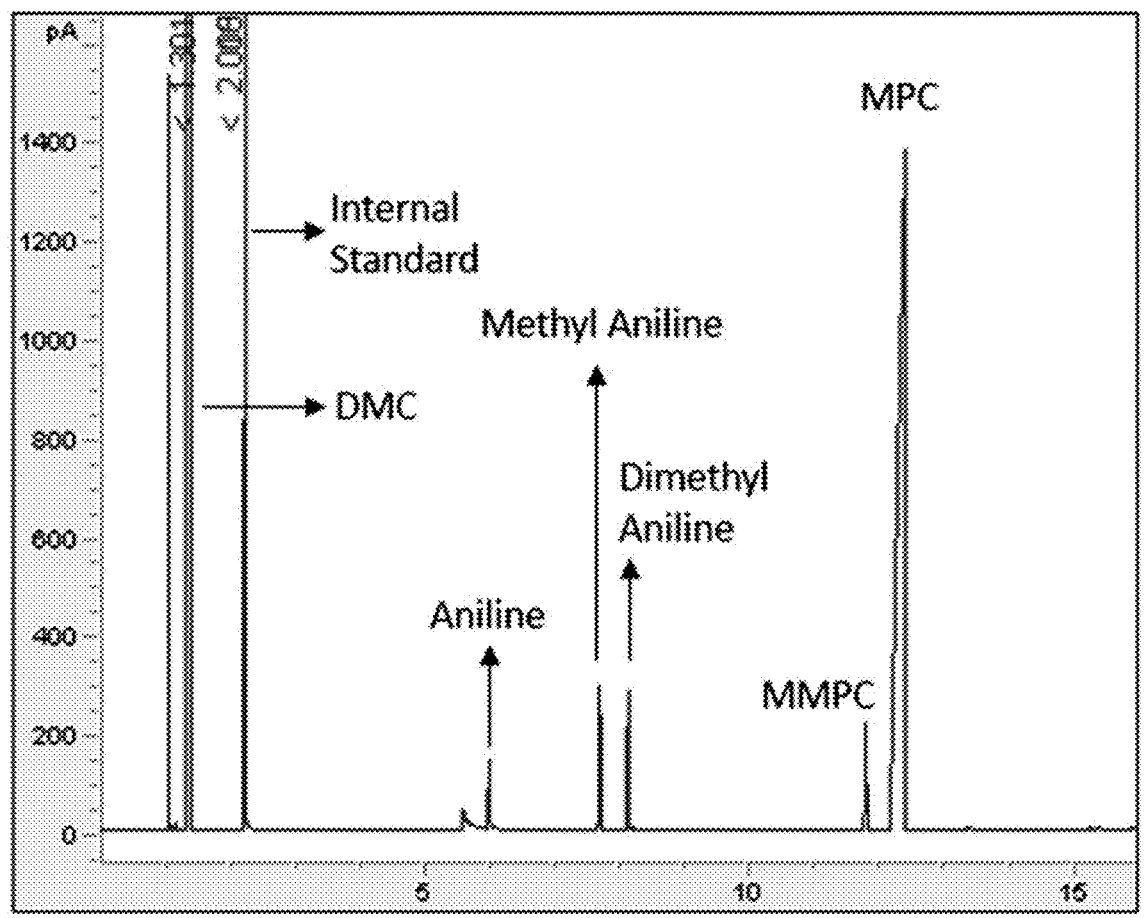
FIG. 4 shows the results of gas chromatography for methyl phenyl carbamate (MPC), methyl N-methylphenyl carbamate (MMPC), methyl aniline (MA), and dimethyl aniline (DMA) produced using catalysts prepared in Preparative Examples 1-5.

The reaction mixture in the reactor was analyzed by gas chromatography to determine the conversion rate of the aniline and the yields (%) of methyl phenyl carbamate (MPC), methyl N-methyl phenyl carbamate (MMPC), methyl aniline (MA), and dimethyl aniline (DMA). The results are shown in Table 3 and FIG. 4.

TABLE 3

| | | Conversion of rate | Yields of products (%) | | | |
|---|---|---|---|---|---|---|
| Example No. | Catalyst | aniline (%) | MPC | MMPC | MA | DMA |
| Example 1 | Preparative Example 1 | 97.9 | 95.2 | 1.5 | 0.5 | 0.7 |
| Example 2 | Preparative Example 2 | 98.4 | 96.1 | 1.3 | 0.3 | 0.7 |

TABLE 3-continued

| Example No. | Catalyst | Conversion of rate aniline (%) | MPC | MMPC | MA | DMA |
|---|---|---|---|---|---|---|
| Example 3 | Preparative Example 3 | 98.9 | 96.4 | 1.2 | 0.2 | 1.1 |
| Example 4 | Preparative Example 4 | 99.6 | 96.8 | 1.1 | 0.3 | 0.4 |
| Example 5 | Preparative Example 5 | 98.4 | 96.2 | 1.1 | 0.3 | 0.8 |

Examples 6-9: Production of Methyl N-Phenyl Carbamate (2)

Methyl N-phenyl carbamate was produced in the same manner as in Examples 1-5, except that the zinc-imidazole complex mixed catalysts synthesized in Preparative Examples 6-9 were used.

TABLE 4

| Catalyst | Conversion rate of aniline (%) | MPC | MMPC | MA | DMA |
|---|---|---|---|---|---|
| Example 6 | 95.2 | 66.4 | 0.8 | 1.3 | 1.5 |
| Example 7 | 97.5 | 79.1 | 0.5 | 0.5 | 0.7 |
| Example 8 | 98.9 | 72.3 | 2.3 | 1.8 | 1.4 |
| Example 9 | 99.5 | 70.9 | 2.4 | 3.0 | 2.6 |

Examples 10-14: Production of Methyl N-Phenyl Carbamate Using Different Amounts of the Catalysts (3)

Methyl N-phenyl carbamate was produced in the same manner as in Examples 1-5, except that the zinc-imidazole complex mixed catalysts were added in the amounts shown in Table 5.

The reaction mixtures in the reactors were analyzed by gas chromatography to determine the conversion rates of the aniline and the yields (%) of the products depending on the amounts of the catalysts. The results are shown in Table 5.

TABLE 5

| Example No. | Amount of catalyst (wt % based on the weight of aniline) | Conversion rate of aniline (%) | MPC | MMPC | MA | DMA |
|---|---|---|---|---|---|---|
| Example 10 | 1 | 56.3 | 55.2 | 0.3 | 0.3 | 0.5 |
| Example 11 | 5 | 81.5 | 79.1 | 0.5 | 0.2 | 0.7 |
| Example 12 | 10 | 99.4 | 98.4 | 1.3 | 0.2 | 0.5 |
| Example 13 | 15 | 99.5 | 95.2 | 2.1 | 0.2 | 1.2 |
| Example 14 | 20 | 99.5 | 94.8 | 2.2 | 0.2 | 2.3 |

Examples 15-19: Production of Methyl N-Phenyl Carbamate for Different Reaction Times (4)

Methyl N-phenyl carbamate was produced in the same manner as in Examples 1-5, except that the reaction time was changed as shown in Table 6.

The reaction mixtures in the reactors were analyzed by gas chromatography to determine conversion rates (%), yields (%), and selectivities (%) depending on the reaction time. The results are shown in Table 6.

TABLE 6

| Example No. | Reaction time (h) | Conversion rate of aniline (%) | MPC | MMPC | MA | DMA |
|---|---|---|---|---|---|---|
| Example 15 | 0.5 | 32.8 | 32.4 | 0.1 | 0.1 | 0.2 |
| Example 16 | 1 | 70.6 | 69.1 | 0.1 | 0.2 | 0.2 |
| Example 17 | 2 | 99.6 | 98.3 | 1.1 | 0.2 | 1.2 |
| Example 18 | 3 | 99.7 | 97.4 | 1.7 | 0.2 | 2.4 |
| Example 19 | 5 | 99.6 | 96.1 | 2.8 | 0.2 | 1.5 |

From the results in Table 6, it can be concluded that the yield of methyl N-phenyl carbamate gradually increases with increasing reaction time. The yield was above 70% from when the reaction time reached 2 h.

Examples 20-24: Production of Methyl N-Phenyl Carbamate at Different Reaction Temperatures (5)

Methyl N-phenyl carbamate was produced in the same manner as in Examples 1-5, except that the reaction temperature was changed as shown in Table 7.

The reaction mixtures in the reactors were analyzed by gas chromatography to determine conversion rates (%), yields (%), and selectivities (%) depending on the reaction temperature. The results are shown in Table 7.

TABLE 7

| Example No. | Reaction temp. (° C.) | Conversion rate of aniline (%) | MPC | MMPC | MA | DMA |
|---|---|---|---|---|---|---|
| Example 20 | 100 | 15.4 | 15.4 | 0.1 | 0.2 | 0.1 |
| Example 21 | 150 | 40.2 | 39.9 | 0.1 | 0.2 | 1.0 |
| Example 22 | 190 | 78.9 | 77.3 | 0.7 | 0.2 | 1.7 |
| Example 23 | 220 | 99.5 | 96.8 | 1.8 | 0.2 | 1.7 |
| Example 24 | 250 | 99.5 | 97.3 | 2.5 | 0.2 | 0.5 |

As can be seen from the results in Table 7, the reaction did not proceed thermodynamically at reaction temperatures of 90° C. or below. The temperature of 150° C. was sufficient for the reaction to proceed kinetically.

Examples 25-29: Production of Methyl N-Phenyl Carbamate Using Mixtures of Two Zinc-Imidazole Complexes in Different Ratios (6)

Methyl N-phenyl carbamate was produced in the same manner as in Examples 1-5, except that mixtures of Zn(benzimidazole)$_2$ synthesized by reaction of ZnC12 and benzimidazole in a ratio of 1:2 and Zn(benzimidazoleXOAc) synthesized by reaction of Zn(OAc)$_2$ and benzimidazole in a ratio of 1:1 were used in the weight ratios shown in Table 8.

Comparative Examples 1-2: Production of Methyl N-Phenyl Carbamate Using Single Zinc-Imidazole Complex Catalyst (7)

Methyl N-phenyl carbamate was produced in the same manner as in Example 25, except that a single zinc-imidazole complex catalyst was used as shown in Table 8.

TABLE 8

| Example No. | Zn(Benzimidazole) (OAc):Zn(Benzimidazole)$_2$ | Conversion rate of aniline (%) | Yields of products (%) | | | |
|---|---|---|---|---|---|---|
| | | | MPC | MMPC | MA | DMA |
| Example 25 | 0.2:0.8 | 97.5 | 71.6 | 6.3 | 7.9 | 8.7 |
| Example 26 | 0.4:0.6 | 98.9 | 72.3 | 5.2 | 11.3 | 8.1 |
| Example 27 | 0.5:0.5 | 98.6 | 89.6 | 3.1 | 2.5 | 3.4 |
| Example 28 | 0.6:0.4 | 97.7 | 68.2 | 4.2 | 13.9 | 7.8 |
| Example 29 | 0.8:0.2 | 96.4 | 48.1 | 3.4 | 11.8 | 12.8 |
| Comparative Example 1 | 0:1 | 95.7 | 67.3 | 7.7 | 8.4 | 9.3 |
| Comparative Example 2 | 1:0 | 95.0 | 46.4 | 4.5 | 13.3 | 7.2 |

Test Example 1: Analysis of Lifetimes of the Zinc-Amine Complex Mixed Catalysts

The procedure of Example 1 was repeated four times to determine the lifetimes of the catalysts. Specifically, after the lapse of 2 h, the reaction was stopped and analysis was performed for methyl N-phenyl carbamate. Thereafter, fresh dimethyl carbonate and aniline were placed in a batch reactor containing the catalyst. The experiment was conducted in quadruplicate. The results are shown in Table 9 and FIG. 5.

TABLE 9

| Number of reuses | Conversion rate of aniline (%) | Yields of products (%) | | | |
|---|---|---|---|---|---|
| | | MPC | MMPC | MA | DMA |
| 1 | 99.5 | 96.3 | 1.3 | 0.3 | 1.6 |
| 2 | 99.4 | 98.2 | 1.2 | 0.2 | 0.2 |
| 3 | 98.7 | 98.7 | 1.1 | 0.1 | 1.2 |
| 4 | 98.3 | 97.4 | 1.3 | 0.2 | 0.6 |
| 5 | 97.9 | 98.0 | 1.1 | 0.2 | 1.4 |

Figure 5:
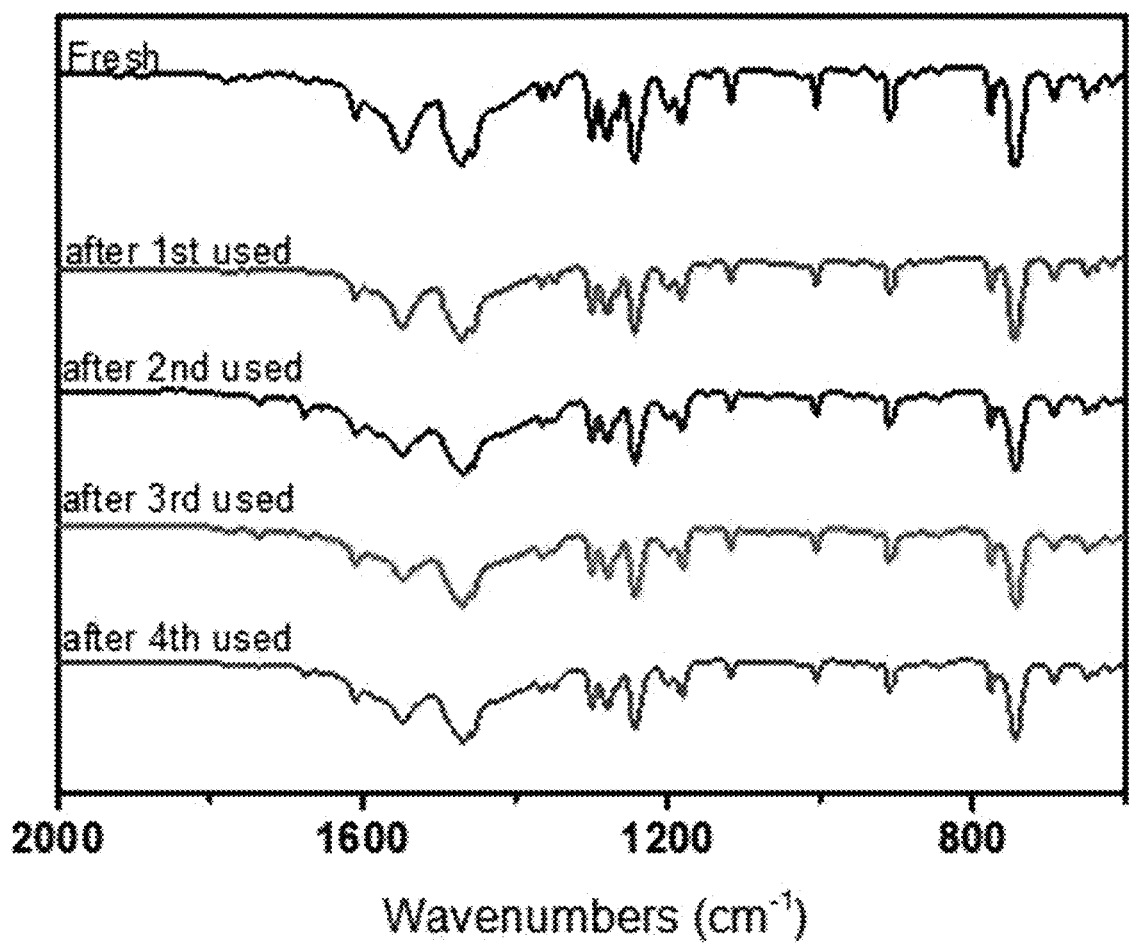
FIG. 5 shows IR spectra of a zinc-imidazole complex mixed catalyst after repeated use 1-4 times.

The results in Table 9 and FIG. 5 demonstrate the fact that methyl N-phenyl carbamate can be produced in high yields in the presence of the inventive zinc-imidazole complex mixed catalyst despite repeated use of the catalyst. These results lead to the conclusion that the use of the inventive catalyst enables the production of methyl N-phenyl carbamate in high yield and can provide a solution to the problems encountered in conventional methods using zinc acetate (Zn(OAc)$_2$), which could not be reused due to its poor activity after repeated use.

What is claimed is:

1. A method for producing a methyl N-phenyl carbamate, comprising:
   (a) preparing a zinc-imidazole complex mixed catalyst, comprising:
      (i) reacting a zinc precursor with an imidazole precursor to provide a reaction mixture; and
      (ii) activating the reaction mixture to prepare the zinc-imidazole complex mixed catalyst which zinc-imidazole complex mixed catalyst-comprises:
      a first zinc-imidazole complex represented by Formula 1:

$$Zn(A)_{x'} \qquad (1),$$

where A is represented by Formula 3 or Formula 4:

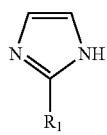
   (3)

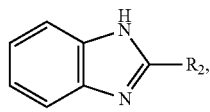
   (4)

where $R_1$ and $R_2$ may be identical to or different from each other, $R_1$ is a chloromethyl group, a phenyl group or a carboxyl group, $R_2$ is a hydrogen atom, a methyl group, a chloromethyl group, a phenyl group or a carboxyl group, and x' is a rational number from 1 to 2, and a second zinc-imidazole complex represented by Formula 2:

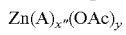
   $$Zn(A)_{x''}(OAc)_y \qquad (2),$$

where A is as defined in Formula 1 and x" and y may be identical to or different from x' and are each independently a rational number from 1 to 2; and
   (b) reacting an optionally substituted phenyl amine with dimethyl carbonate in the presence of the zinc-imidazole complex mixed catalyst to provide said methyl N-phenyl carbamate.

2. The method according to claim 1, wherein reacting the optionally substituted phenyl amine with dimethyl carbonate is carried out at a temperature of 100 to 250° C. for 1 to 5 hours.

3. The method according to claim 1, wherein the optionally substituted phenyl amine is reacted with the dimethyl carbonate in a molar ratio of optionally substituted phenyl amine:dimethyl carbonate of 1:5 to 1:40.

4. The method according to claim 1, wherein the zinc-imidazole complex mixed catalyst is present in an added amount of 1 to 20% by weight based on the weight of the optionally substituted phenyl amine.

5. The method according to claim 1, wherein the optionally substituted phenyl amine is selected from the group consisting of aniline, phenylenediamine, methylenediphenyldiamine, toluenediamine, and mixtures thereof.

* * * * *